Figure 1:
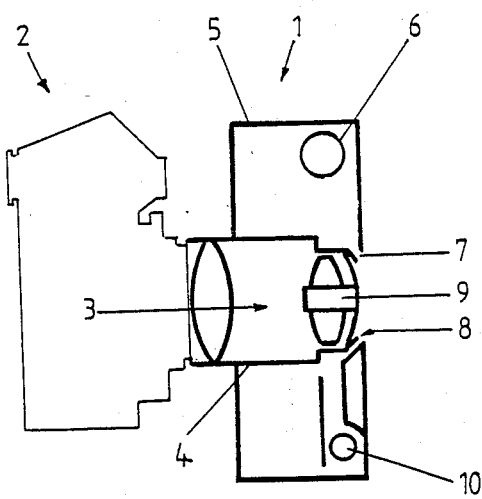

United States Patent [19]

Molteno

[11] Patent Number: 4,586,796

[45] Date of Patent: May 6, 1986

[54] TESTING TO DETERMINE THE FIXATION AND FOCUSING OF LIVING EYES

[76] Inventor: Anthony C. B. Molteno, 9 Fairfax Street, Maori Hill, Dunedin, New Zealand

[21] Appl. No.: 539,825

[22] Filed: Oct. 7, 1983

[30] Foreign Application Priority Data

Oct. 8, 1982 [NZ] New Zealand ............... 202116

[51] Int. Cl.$^4$ ............... A61B 3/14; A61B 3/10
[52] U.S. Cl. ............... 351/206; 351/214
[58] Field of Search ............... 351/206, 207, 208, 214; 354/62

[56] References Cited

U.S. PATENT DOCUMENTS

| | | | |
|---|---|---|---|
| 3,762,803 | 10/1973 | Papritz | 351/214 X |
| 3,944,342 | 3/1976 | Martnex | 351/214 X |
| 4,171,877 | 10/1979 | Karasawa et al. | 351/214 X |
| 4,331,392 | 5/1982 | Sato | 351/214 |

Primary Examiner—Rodney B. Bovernick
Attorney, Agent, or Firm—Ladas & Parry

[57] ABSTRACT

A visual image screener for determining abnormality in living eyes particularly of infants and small children which has essential components of:

(1) A light source consisting of a narrow annular reflector illuminated by an electronic flash tube.

(2) A special photographic objective lens in which the first component of the lens is the limiting aperture of the system.

(3) A flashing fixation light placed exactly on the optical axis.

These components are assembled with the annular reflecting light source surrounding the camera objective so that the inner sharp edge of the reflector forms the limiting aperture of the entire lens system. The first component of the lens is perforated to permit the fixation light to be mounted in the optic axis and in the same plane as that occupied by the reflecting annulus or slit. These components are mounted on a standard single lens reflex camera body with a focal plane shutter. When this apparatus is used to photograph in color the face of the subject being tested who is both emmetropic and fixing the flashing fixation target, the resulting picture shows symmetrically placed corneal reflexes and pupillary apertures which are either dark or show deep red fundal reflex. However, eyes which do not fix the target show both deviation of the corneal light reflex and a brightening and change of color from deep red through yellow to white of the fundal reflex. Fixing eyes with significant refractive error show brightening in color change of the fundal reflex without displacement of the pupillary reflex.

11 Claims, 4 Drawing Figures

TESTING TO DETERMINE THE FIXATION AND FOCUSING OF LIVING EYES

This invention relates to the determination of the fixation and focusing of living eyes, for example in the examination or treatment of small children with squint or refractive errors. The test is visually recorded and while in this specification the medium for such visual recording is photographic, the invention is intended to cover any visual image recording means, for example, electronic means such as the video tapes.

BACKGROUND

In the past photographic determination of optical defects has been utilised,
1. a light source mounted alongside a camera objective; and
2. a light source together with a fibreoptic light guide mounted in the camera objective.

In the first technique (Kaakinin's) the sensitivity is limited by the distance between light source and the optical edge of the camera lens used.

In the second technique (Braddick's) the sensitivity is limited by the thickness of the cladding which must surround the fibreoptic and also by the fibreoptic blocking off a portion of the lens.

In both Kaakinin's and Braddick's testing techniques an infant's attention is attracted to a flashing fixation light which is placed on or next to the camera objective and in some of the later experiments on the optic axis. Once the infant's attention is attracted an electronic flash is emitted from, one or two small flash tubes at right angles in Kaakinin's technique, or a single fibreoptic source mounted on the optic axis of the camera and in front of the objective in Braddick's technique.

In either case light travels from the source and is focused on the retina of the subject's eyes. If the eyes are optically good and are focused on or very close to the source then the retina image of the source is sharply defined. Light is reflected from two layers of the retina; the vitreo retinal interface and after passing through the retina a layer of brown pigment at Bruch's membrane. There is relatively little lateral diffusion of light in passing through these layers and so light reflected from both layers is passed back along the pathways by which it came to form a sharply defined image of the source exactly superimposed on the flash tube or fibreoptic from which it originated. In either case light from these layers is prevented from passing into the camera lens. In such a case a colour photograph taken of the subject's face will either show dark pupils or a dark red illumination of the pupillary aperture. This is due to the light passing through the retina and pigment cell layer and being widely scattered by the blood in the choroid before being reflected back towards the pupil from the inner layers of the sclera. This red reflex is very dim or absent in heavily pigmented eyes and relatively bright in blonde subjects but in all cases coloured a deep red by the choroidal blood and quite easily to distinguish from the lighter coloured reflexes from more superficial layers.

In the case of an eye which has a refractive error or which is not focused on the source of the light the retinal image is enlarged by being defocused so that the light reflected from the vitreo retina interface and Bruch's membrane forms an enlarged defocused image and is reflected back towards the source.

If this defocusing is sufficient for light to enter the edge of the camera lens (Kaakinin) or bypass the centre fibreoptic source (Braddick) then light from these superficial retinal structures enters the camera lens and produces a bright yellow or white appearance of the pupillary aperture in a colour photograph of the subject's face.

The sensitivity of both of these methods depends on the diameter of the subject's pupil and the angular distance between the light source and the clear edge (external Kaakinin or internal Braddick) of the camera objective. The sensitivity of the Kaakinin's technique is limited by the distance between the optic centre of the flash units and the optical edge of the camera lens employed. The sensitivity of the Braddick technique is limited by the thickness of the low refractive index cladding surrounding the fibreoptic source employed.

Both Kaakinin and Braddick's technique can be considered as crude forms of null test. Null tests are, in very broad terms, tests which in good optical systems when tested, allows no light to pass or else passes light evenly through all areas of its aperture.

THE PRESENT INVENTION

The present invention is an application of a more refined form of null test to the problem of determining whether or not an infant is fixing and focusing on an object with both eyes simultaneously. In this application the two light sources placed at right angles to each other of Kaakinin and the single central light source of Braddick are replaced by a very narrow light source which extends around the entire or almost the entire circumference of a camera objective which is so constructed that the opaque backing to this annular slit constitutes the limiting aperture of the camera's lens. With this device a very slight degree of defocusing of the subject's eye with a corresponding small degree of defocusing of the light rays returned to the source allows light reflected from the superficial layers of the retina to enter the camera lens and cause a change in colour and brightening of the pupil of the subject that is being photographed.

With the increased sensitivity provided by this development it has been found necessary to place the fixation light exactly on the optic axis and in the plane of the slit.

The advantages of providing a narrow slit of light source combined with the aperture stop for the objective lens are:

(1) It is possible to reduce the distance between the light source and the camera lens aperture so much that subjects can be photographed at a distance of around 50 cm while retaining adequate sensitivity. This short distance is most important in the cases of infants and small children whose attention can only be well held by near objects.

(2) By increasing the length of the slit to that of the circumference of the lens it becomes possible to pass sufficient light through the slit with a simple portable ring flash driven by a portable power source.

(3) Certain astigmatic errors are made evident. In addition an indication of the direction of the axis of the cylindrical lens needed for their correction is given.

Theoretically the full sensitivity of which this technique is capable would be obtained by utilising an extremely narrow slit. A diffraction limited slit for a working distance of 50 cm would have a width of 0.0073 mm. In addition, it will be apparent that the light which gives the appearance of the brightening of the pupil in defective eye cases passes through the very edge of the lens in the first instance so that small errors could in theory be made more evident by stopping out the centre of the lens and leaving the annulus remaining to transmit light.

In practice it is considered an advantage to have this system somewhat less sensitive than may be optimised so that as the reflected light becomes increasingly defocused a progressive encroachment of these light rays upon the lens occurs with a gradual and progressive brightening of the pupillary reflex which corresponds in some degree to the degree of refractive error present.

Compromises which have been made in practice to take into account the factors discussed above are set out as follows. It should be recognised however that this is an example only of the way in which the invention may be reduced to practice and is not intended to be limiting.

(1) A widening of the slit to 0.5 mm which reduces the sensitivity but allows more light to pass.

(2) The adoption of a clear aperture for the camera objective of 14 mm. The reason for this choice is highlighted by reference to a larger diameter lens, for example of 30 mm. If this lens was used to photograph a subject whose refractive error defocused the returning rays so that they overlapped by 2 mm they would be passing through an outer zone of 2 mm of the lens which is a very small percentage of the clear aperture of the lens which would be receiving light from the subject's face which is necessarily also illuminated by the same electronic flash passing through the slit. This would mean that the light intensity would have to be reduced in order to avoid overexposure of the subject's face. In this situation it is likely that the light returning from within the eye would be insufficiently bright to affect the film. On the other hand, a 2 mm zone around the periphery of a lens of 14 mm clear diameter contains some 25% of its area. This proportion is increased where a central stop is used. However, reduction of the diameter of the camera objective lens reduces the overall length of the slit through which the flash light will be illuminate and which in accordance with this invention, must be placed around the circumference as detailed previously.

(3) The focal length of the camera objective is a compromise between adequate image size, the speed necessary for correct exposure with the light available and the need for reasonable depth of focus.

These conflicting factors have been resolved in one possible combination which as indicated above, should not be identified as limiting but merely illustrative as follows:

(1) An effective slit width of 0.5 mm.

(2) A diameter of the inner edge of the slit which is also the aperture stop of the camera lens of 14 mm.

(3) A focal length of the camera lens of 67 mm.

The apparatus as detailed previously is intended for use with a 35 mm single lens reflex camera body.

DRAWING DESCRIPTION

Figure 2:
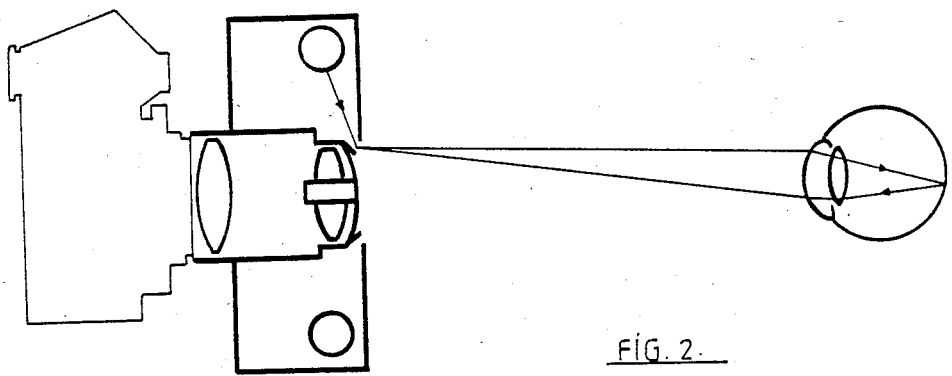
Figure 3:
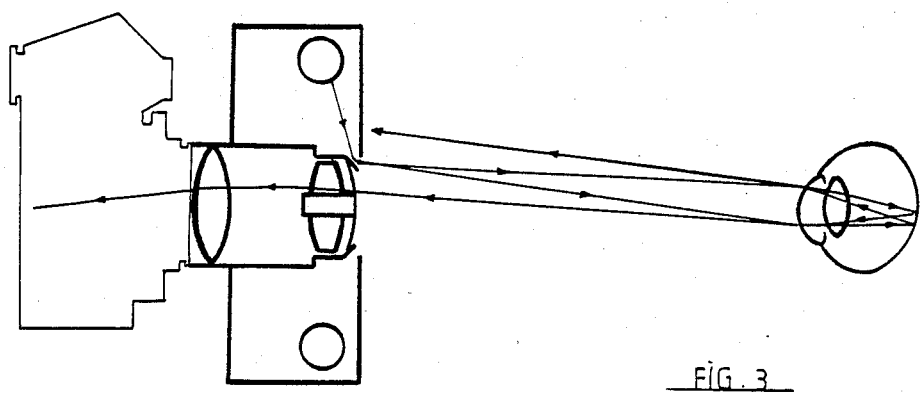
Figure 4:
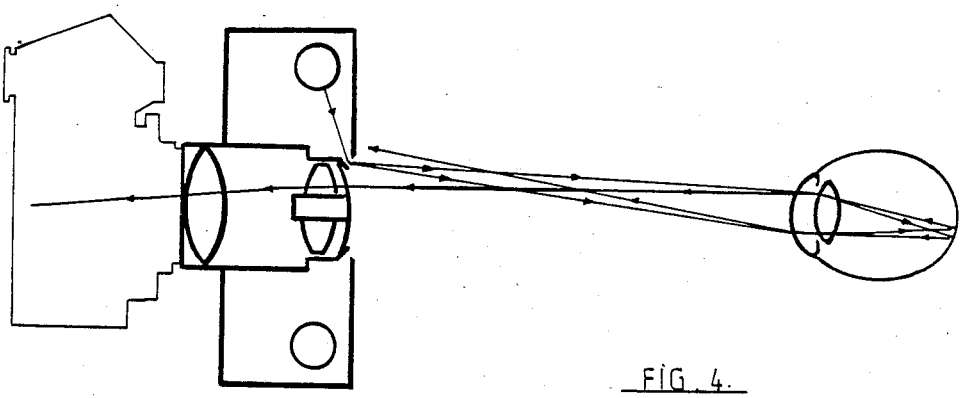

FIG. 1 diagrammatically represents the present invention,

FIG. 2 shows the path of light rays in an emmetropic eye focused on the fixation light, FIG. 3 shows the path of light rays in a hypermetropic eye unable to focus on the fixation light, and FIG. 4 illustrates the path of light rays in a myopic eye unable to focus on the fixation light.

PREFERRED EMBODIMENT

The apparatus employed in the present invention is diagrammatically represented in the accompanying drawings and is adapted to be associated with a 35 mm single reflex camera 2 although as has been previously pointed out the invention may be adapted to be used in association with other visual image reproducing means.

The objective lens system 3 or camera objective is mounted in a suitable housing 4 about which was supported a further housing 5 in which is mounted a flash tube 6, for example, a three inch sun burst flash tube.

A slit 7 surrounding the front lens of the camera objective provides the light source with the inner edge 8 of the reflector defining the slit forming the limiting aperture of the camera objective and also forming a sharp edge between the camera objective and the light source. The inner surface of the housing 5 is treated to ensure a maximum light emission through the light slit and this can be achieved using known techniques of light guides or reflective inner surfacing. In FIG. 1 the flash tube in the top part of the diagrammatic representation is shown positioned to impinge on the reflective surface adjacent the slit and produce the slit of light. In the lower half of FIG. 1 the light tube is shown located to be associated with a plastic light guide 10 transmitting light to the slit. In either case the angle of light emergence should be sufficient to cover the face of the subject.

A flashing fixation or location light is positioned on the optical axis and in the same plane as the slit. This location light is intended to attract and hold the attention of young children. It may also be accompanied by an electronic squeak or other audio signal to serve in the same manner. The duration of each flash while not critical may be, by way of example, 0.5 seconds with 0.25 second intervals. This light is preferably centrally located in the front lens of the objective thus also serving to blank out the centre of the lens to make the system more sensitive to light entering towards the outer perimeter of the lens as discussed above.

The width of the slit is 0.5 mm although the range of the slit width can be from 0.0073 to 2 mm.

The aperture of the camera objective is 14 mm although a usable range would be from 5 mm to 25 mm.

The focal length of the camera objective is 67 mm but a useful range would be from 50 to 100 mm. The various considerations which are relevant in selecting the operating perimeters of the apparatus have been discussed previously.

In order to use the present invention the apparatus is attached to the camera and the focus of the camera is adjusted for a fixed subject distance of, for example, 50 cm. The distance is a matter of choice and could be extended considerably beyond the 50 cm up to, for example, 2 meters but again for the reasons previously discussed it is preferable to use the closer distance to ensure a greater attention of the subject particularly with young children. The photographs are taken in subdued light to allow a moderate degree of pupillary dilation (mydriatics are not used).

The subject's attention is attracted when the flashing fixation light and audio signal are activated. On a single photograph being taken the flash is activated emitting light through the slit from the sun burst flash tube and the shutter in the camera operated in the normal manner. A Kodak high speed Ektachrome colour film (500ASA) is used and is developed and mounted for projection.

In the case of a subject with emmetropic eyes, focused accurately on the fixation light at the moment of taking the photograph, the light from the slit forms a sharply focused image on the retina and is reflected back at the vitreo retinal interface and Bruch's membrane to form a second real image exactly superimposed on the slit. In this case, light reflected from the retina does not enter the camera lens and the fundal reflexes of the subject are either not registered (i.e. the pupillary apertures appear dark) or photographed as a dull red due to light passing through the pigment epithelium and being widely scattered in the choroid before reflected by the sclera in subjects with lightly pigmented fundi.

In the case of a subject in whom one or both eyes are not focused correctly, the retinal image of the slit is out of focus and the secondly image no longer exactly superimposed on the slit, so that light reflected from the retinal structure is no longer completely cut off by the knife boundary between the slit and the camera objective and light enters the camera objective. Under these circumstances the subject is photographed with a bright yellow or white fundal reflex in the pupil of the defective eye.

Since the focusing of the eye is being tested depends on the accuracy of the subject's fixation reflexes and the retina is a complex structure reflecting light from several layers, clinical trials have been undertaken to determine the practical utility of the apparatus and method as previously disclosed.

Over 1000 children between the ages of six months and 15 years seen for various eye conditions at the University of Otago Outpatients Clinic were photographed with the present apparatus.

The subjects were identified by a gummed label on their foreheads and sat facing the camera in subdued room light. The completed records thus included identification information which, from an administrative point of view, is most significant.

The photographs were classified blind (i.e. without knowledge of clinical findings) by simple inspection of the projected image into normal, borderline and abnormal groups which were compared with the results of the clinical examination which included fundoscopy, orthoptic work up and cycloplegic refraction in the majority of cases.

The criteria for photographic normality were taken to be:
(1) Either absence of uniformly deep red fundal reflexes of equal brightness in each eye.
(2) Equal pupillary size.
(3) A symmetrical near central position of the corneal light reflexes.
(4) Absence of ptosis, coloboma, heterochromia or other visible defect.

The criteria for borderline abnormality were taken as doubt on any of the above points while definite abnormality was taken to be present if:
(1) Individual fundal reflexes showed uneven distribution of colour or brightness; or a defined difference in colour or brightness was present in comparing the two eyes.
(2) Unequal pupillary size.
(3) Asymmetrical position of the corneal light reflexes.
(4) Presence of ptosis or other visible defects.

The co-relation between the photographic and clinical classification showed that the photographic classification does in fact identify abnormalities. There is a slight tendency for clinically normal children to be classified as abnormal or borderline due to their not fixing on the target as the photograph was taken. However, out of the more than 1000 subjects tested no serious abnormality has been missed by the test employing the present invention. Two cases with only slight abnormality were not identified in the test and were classified photographically as normal. The results have shown the co-relation between photographic and clinical classification is approximately 90% with the error in co-relation mainly attributable to the normal child not fixing the target fixation light as the photograph was taken.

The results of the trial confirm that it would be possible for a minimally trained person to photograph infants and send the film in for development and interpretation by an ophthalmologist who is thus able to "screen infants" at a rate of around 60 per hour using a test which is of the same order of sensitivity as expert clinical examination with atropine refraction. The present invention thus ensures there is no longer any scientific or economic obstacle to the identification of all cases of refractive error or squint at an early age when treatment is most likely to be effected and consequently the present invention represents a significant and important development in this field of technology.

What is claimed is:

1. A method of determining the fixation and focusing of living eyes, said method comprising the steps of providing a flash of light from a slit light source substantially surrounding a camera objective, said slit light source and said camera objective being separated by a sharp edge, and providing an eye fixation light at the optical axis of the camera objective and in substantially the same plane as the slit light source, and recording the light entering the camera objective on visual image reproducing means so that in use, when the eyes of a subject are focused on the fixation light the path of the light rays from the slit light source through the subject's eyes to focus on the retina and back form a retinal image of the slit which image, if not correctly focused by the eyes being tested, enters light through the camera objective to be recorded a brightening in the pupils of the defective eye and thereafter inspecting the visual image reproducing means to determine whether the pupils appear brightened.

2. A method as claimed in claim 1 wherein the light emerges as a flush from the slit evenly around the camera objective and with sufficient intensity to illuminate and allow a photographic reproduction of the subject's face.

3. A method as claimed in claim 1 wherein the fixation light is a flashing light augmented by an audio signal to attract the subject's attention.

4. A method as claimed in claim 1 wherein administrative and identification information are attached to the subject's forehead prior to the visual image being recorded.

5. Apparatus for use in determining the fixation and focussing of living eyes, said apparatus comprising a camera housing, a camera objective mounted in said camera housing, means to form a circular illuminable slit around said camera objective with the inner edge of the illuminable slit providing the limiting aperature of the camera objective and also forming a sharp edge between the camera objective and any light projected through said slit, a flash light source around the camera objective to illuminate the slit, a fixation light on the optic axis of the camera objective and in the same plane as the slit visual image recording means to record light passing through said camera objective operable in association with said flash light source which illuminates said slit so that when said eyes are focussed on the fixation light, light from the slit slight source focusses on the retina of the eyes and is reflected to form a retinal image of the slit whereby if the eyes being tested do not focus correctly, light passes through the camera objective to be recorded as a brightening in the pupils of the defective eye on the visual image recording means.

6. An apparatus as claimed in claim 5 wherein the width of the slit is between 0.0073 and 2 mm.

7. An apparatus as claimed in claim 5 wherein the camera objective has an aperture in advance of the first lens of between 5 mm and 25 mm in diameter.

8. An apparatus as claimed in claim 5 wherein the focal length of the objective lens is between 50 mm and 100 mm.

9. An apparatus according to claim 6 wherein said slit width is about 0.5 mm.

10. An apparatus according to claim 7 wherein said aperture diameter is about 14 mm.

11. An apparatus according to claim 8 wherein the focal length of the objective lens is about 67 mm.

* * * * *